US007217525B2

(12) United States Patent
Worley et al.

(10) Patent No.: US 7,217,525 B2
(45) Date of Patent: May 15, 2007

(54) METHOD FOR IDENTIFYING COMPOUNDS WHICH AFFECT IONOTROPIC GLUTAMATE RECEPTOR AGGREGATION

(75) Inventors: Paul Worley, Baltimore, MD (US); Richard O'Brien, Baltimore, MD (US); DeSheng Xu, Towson, MD (US); Richard L. Huganir, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 512 days.

(21) Appl. No.: 10/299,957

(22) Filed: Nov. 18, 2002

(65) Prior Publication Data

US 2003/0232776 A1 Dec. 18, 2003

Related U.S. Application Data

(63) Continuation of application No. 09/328,710, filed on Jun. 9, 1999, now abandoned.

(51) Int. Cl.
G01N 33/567 (2006.01)
G01N 33/53 (2006.01)
C12Q 1/68 (2006.01)

(52) U.S. Cl. .......................... 435/7.1; 435/6; 435/7.21

(58) Field of Classification Search ...................... None
See application file for complete search history.

(56) References Cited

OTHER PUBLICATIONS

Garlanda et al. Annu. Rev. Immunol. 2005. 23:337-66.*
Goodman et al. Cytokine & Growth Factor Rev. 1996. 7: 191-202.*
Bottazzi et al. J. Biol. Chem. 1997. 272:32817-32823.*
Scott et al. Nature Genetics, 1999, 21:440-443.*
Bowie et al., "Deciphering the Message in Protein Sequences: Tolerance to Amino Acid Substitutions." Science, vol. 247: 1306-10, Mar. 1990.*
Ngo et al., "Computational Complexity, Protein Structure Prediction, and the Levinthal Paradox." The Protein Folding Problem and Tertiary Structure Prediction: 491-495, 1994.*
Frommel et al., "An Estimate on the Effect of Point Mutation and Natural Selection on the Rate of Amino Acid Replacement in Proteins." J. Mo. Evol., vol. 21: 233-257, 1985.*
O'Brien, et al., "Synaptic Clustering of AMPA Receptors by the Extracellular Immediate-Early Gene Product Narp," Neuron 23 (2):309-323 (1999).
Tsui, et al., "Narp, a Novel Member of the Pentraxin Family of Proteins that is Synthesized, Secreted and Active as a Monomeric Molecule," Society of Neuroscience Abstracts. 26 Annual Meeting (Washington, DC) 22:(Part I of 3):p. 299, Abstract No. 125 (1996).
Tsui, et al., "Narp, a Novel Member of the Pentraxin Family, Promotes Neurite Outgrowth and Is Dynamically Regulated by Neuronal Activity," The Journal of Neuroscience, 16 (8):2463-2478 (1996).

* cited by examiner

Primary Examiner—Janet L. Andres
Assistant Examiner—Chang-Yu Wang
(74) Attorney, Agent, or Firm—DLA Piper US LLP

(57) ABSTRACT

A method is provided for identifying a compound which affects the formation of AMPA receptors into aggregates. The method also provides for a compound, for example, a long pentraxin polypeptide or fragment thereof, having a pentraxin binding domain and affecting AMPA receptor aggregation. The method provided herein affects AMPA receptor aggregation of GluR1, GluR2 and GluR3 receptor subunits.

9 Claims, 2 Drawing Sheets

SEQUENCE LISTING

<160> NUMBER OF SEQ ID NOS: 2

<210> SEQ ID NO 1
<211> LENGTH: 2569
<212> TYPE: DNA
<213> ORGANISM: Rattus norvegicus
<220> FEATURE:
<221> NAME/KEY: CDS
<222> LOCATION: (128)...(1423)

<400> SEQUENCE: 1

-continued

```
tggtgctggc gtttccctgc ttgcacgcgg ttccctcgag cgccgctccg accgacgtag      60
ccggccgcga aggcgcccag acggcaagcc agcgacccat gctgaagtga gcgcccaggt     120 cagcgag atg ctg gcg ctg ctg acc gcc ggc gtg gcg ctc gcc gtg gcc      169
        Met Leu Ala Leu Leu Thr Ala Gly Val Ala Leu Ala Val Ala
        1               5                   10 gcg gga caa gcc cag gat aac ccg ata cct ggc agt cgc ttc gtg tgc      217
Ala Gly Gln Ala Gln Asp Asn Pro Ile Pro Gly Ser Arg Phe Val Cys
15                  20                  25                  30 acc gcg ctg ccc ccc gaa gcg gcg cgc gcc ggc tgc ccg ctc ccc gcg      265
Thr Ala Leu Pro Pro Glu Ala Ala Arg Ala Gly Cys Pro Leu Pro Ala
                35                  40                  45 atg ccc atg cag gga ggc gcg ctg agc cct gag gag gag ctg cga gcc      313
Met Pro Met Gln Gly Gly Ala Leu Ser Pro Glu Glu Glu Leu Arg Ala
        50                  55                  60 gct gtg ctg cac tgg cgc gag acc gtc gtg cag cag aag gag acg ctg      361
Ala Val Leu His Trp Arg Glu Thr Val Val Gln Gln Lys Glu Thr Leu
        65                  70                  75 ggc gct cag cga gaa gcc atc cga gaa ctc acc agc aag ctg gcc cgc      409
Gly Ala Gln Arg Glu Ala Ile Arg Glu Leu Thr Ser Lys Leu Ala Arg
80                  85                  90 tgt gag gga cta gcc ggc ggt aag gcg cgc ggc acg ggg gcc acg ggc      457
Cys Glu Gly Leu Ala Gly Gly Lys Ala Arg Gly Thr Gly Ala Thr Gly
95                  100                 105                 110 aag gac acc atg ggc gac ctg ccg cgg gac ccg ggc cac gtc gtg gag      505
Lys Asp Thr Met Gly Asp Leu Pro Arg Asp Pro Gly His Val Val Glu
                115                 120                 125 cag ctt agc cgc tcg ctg cag acc ctc aag gac cgc ttg gag agc ctc      553
Gln Leu Ser Arg Ser Leu Gln Thr Leu Lys Asp Arg Leu Glu Ser Leu
        130                 135                 140 gag ctc caa ctc cac acc aac gcg tct aat gcc ggg ctg ccg agc gac      601
Glu Leu Gln Leu His Thr Asn Ala Ser Asn Ala Gly Leu Pro Ser Asp
        145                 150                 155 ttc cga gag gtg ctc cag cgg agg ctg ggg gag ctg gag agg cag ttg      649
Phe Arg Glu Val Leu Gln Arg Arg Leu Gly Glu Leu Glu Arg Gln Leu
160                 165                 170 cta cgc aag gtg gcc gag ctg gaa gac gag aag tcc ctg ctc cac aat      697
Leu Arg Lys Val Ala Glu Leu Glu Asp Glu Lys Ser Leu Leu His Asn
175                 180                 185                 190 gag acc tcg gct cac cgg cag aag aca gag aac aca ctg aat gca ctg      745
Glu Thr Ser Ala His Arg Gln Lys Thr Glu Asn Thr Leu Asn Ala Leu
                195                 200                 205 ctg cag agg gtg act gag ctg gag aga ggc aac agt gca ttc aag tca      793
Leu Gln Arg Val Thr Glu Leu Glu Arg Gly Asn Ser Ala Phe Lys Ser
        210                 215                 220 cca gat gca ttc aaa gtg tcc ctc cct ctc cgt aca aac tac cta tac      841
Pro Asp Ala Phe Lys Val Ser Leu Pro Leu Arg Thr Asn Tyr Leu Tyr
        225                 230                 235 ggc aag atc aag aag acg ttg ccc gag ctg tat gcc ttc acc atc tgc      889
Gly Lys Ile Lys Lys Thr Leu Pro Glu Leu Tyr Ala Phe Thr Ile Cys
240                 245                 250 ctg tgg ctg cgg tcc agc gcc tcg cca ggc atc ggc acg cca ttc tcc      937
Leu Trp Leu Arg Ser Ser Ala Ser Pro Gly Ile Gly Thr Pro Phe Ser
255                 260                 265                 270 tac gct gtg cct ggg caa gcc aat gag att gtg ctg ata gag tgg ggt      985
Tyr Ala Val Pro Gly Gln Ala Asn Glu Ile Val Leu Ile Glu Trp Gly
                275                 280                 285 aac aat ccc ata gag ctg ctt atc aac gac aag gtc gca cag ctg ccc     1033
Asn Asn Pro Ile Glu Leu Leu Ile Asn Asp Lys Val Ala Gln Leu Pro
```

```
                     290                 295                 300
ctg ttt gtc agc gat ggc aag tgg cac cat atc tgc atc acc tgg acc              1081
Leu Phe Val Ser Asp Gly Lys Trp His His Ile Cys Ile Thr Trp Thr
            305                 310                 315 act cga gac ggc atg tgg gaa gca ttc cag gac ggg gag aag ctg ggc              1129
Thr Arg Asp Gly Met Trp Glu Ala Phe Gln Asp Gly Glu Lys Leu Gly
        320                 325                 330 acc ggg gag aac ctg gca ccc tgg cat ccc atc aag cca ggg ggt gtg              1177
Thr Gly Glu Asn Leu Ala Pro Trp His Pro Ile Lys Pro Gly Gly Val
335                 340                 345                 350 ctc atc ctg ggg cag gag cag gac act gtg gga ggc aga ttt gat gcc              1225
Leu Ile Leu Gly Gln Glu Gln Asp Thr Val Gly Gly Arg Phe Asp Ala
                355                 360                 365 aca cag gcc ttc gtt gga gag ctt agc cag ttc aac ata tgg gac cgt              1273
Thr Gln Ala Phe Val Gly Glu Leu Ser Gln Phe Asn Ile Trp Asp Arg
            370                 375                 380 gtc ctc cgg gca caa gag atc atc aac atc gcc aac tgc tcc acg aac              1321
Val Leu Arg Ala Gln Glu Ile Ile Asn Ile Ala Asn Cys Ser Thr Asn
        385                 390                 395 atg cct gga aac atc atc cca tgg gtg gac aac aat gtc gat gtg ttt              1369
Met Pro Gly Asn Ile Ile Pro Trp Val Asp Asn Asn Val Asp Val Phe
400                 405                 410 gga ggg gct tcc aag tgg cct gtg gag acg tgc gaa gag cgt ctc ctg              1417
Gly Gly Ala Ser Lys Trp Pro Val Glu Thr Cys Glu Glu Arg Leu Leu
415                 420                 425                 430 gac ttg tagctacctt ctccctgtcc cagaggccaa gagcgggctg ttctggggag               1473
Asp Leu ttcaaggcat ctattcccga gttcaactaa aatctctggc ctgagtagga aagaaccaga            1533
gcccctaagg caggctgtgt ggcctccttt gtcttaggct cctatgttct tactgctttg            1593
ttctttggtg ggaagtgacc gaagccctgg gaagagtcct gagccacttc ctgctggggt            1653
ttctagtaaa gtctgtgagc ctctccaccc ctcctgtaaa tgctagtgca acccagccct            1713
gcctgtcatt ttggatcctt agtgtctcgt gtgtgcttcc cgtctgtccc ctttgatggc            1773
tgtgtggtca tcctaccggg gtggcctggg tcccttgtgt gtgtagcaca tccctgcttt            1833
tgactgaaca cagtgcacag aagctacccg cccctgaaac agggtctctc cctcagtgtc            1893
atgtgcactc tggtctctcc ctctgagggg actgcagctg ctggagggcc agctgcccag            1953
acagtcccca gcatccccaa agcagaccct ccgccatgga gaaagtcccc cacagcttcc            2013
ccaccctctg tccacctctc agaccccacg cttctaagga ccattgctgg gttggctttc            2073
aaaagctgct gctctcatct ggtgccaaaa gttcatttgc agcttctaca ccgttctgtg            2133
tggtttgggg attgacttta ttcccccaca aaagaggaac agccattaga agccagcctc            2193
ccctcctttt gatgctcagc ccactgtgaa gagtgagctt gcttgtaagc cacattggtt            2253
tctgtgagca tctgactctc ccccgtccag tattttcccc ggaactggag attcgagcct            2313
agttcggctg ctacctgctt agtgactcca ggctgcatca tgtatcataa tttattttaa            2373
agacaaagtg attcagtggg gaaatttata aagctataaa tattatatat tttattttc             2433 atacatgttt aaagtgcgga tccatggatg ttccatttgt aggaccagct tgacgtgccc            2493
atcctgacat tgtatgccac aagagctctt gtgatgatgg aattttgatt aaagtgcact            2553
ggaagatgaa aaaaaa                                                            2569

<210> SEQ ID NO 2
<211> LENGTH: 432
<212> TYPE: PRT
```

<213> ORGANISM: Rattus norvegicus

<400> SEQUENCE: 2

```
Met Leu Ala Leu Leu Thr Ala Gly Val Ala Leu Ala Val Ala Ala Gly
 1               5                  10                  15
Gln Ala Gln Asp Asn Pro Ile Pro Gly Ser Arg Phe Val Cys Thr Ala
             20                  25                  30
Leu Pro Pro Glu Ala Ala Arg Ala Gly Cys Pro Leu Pro Ala Met Pro
         35                  40                  45
Met Gln Gly Gly Ala Leu Ser Pro Glu Glu Leu Arg Ala Ala Val
 50                  55                  60
Leu His Trp Arg Glu Thr Val Val Gln Gln Lys Glu Thr Leu Gly Ala
 65                  70                  75                  80
Gln Arg Glu Ala Ile Arg Glu Leu Thr Ser Lys Leu Ala Arg Cys Glu
                 85                  90                  95
Gly Leu Ala Gly Gly Lys Ala Arg Gly Thr Gly Ala Thr Gly Lys Asp
            100                 105                 110
Thr Met Gly Asp Leu Pro Arg Asp Pro Gly His Val Val Glu Gln Leu
        115                 120                 125
Ser Arg Ser Leu Gln Thr Leu Lys Asp Arg Leu Glu Ser Leu Glu Leu
    130                 135                 140
Gln Leu His Thr Asn Ala Ser Asn Ala Gly Leu Pro Ser Asp Phe Arg
145                 150                 155                 160
Glu Val Leu Gln Arg Arg Leu Gly Glu Leu Glu Arg Gln Leu Leu Arg
                165                 170                 175
Lys Val Ala Glu Leu Glu Asp Glu Lys Ser Leu Leu His Asn Glu Thr
            180                 185                 190
Ser Ala His Arg Gln Lys Thr Glu Asn Thr Leu Asn Ala Leu Leu Gln
        195                 200                 205
Arg Val Thr Glu Leu Glu Arg Gly Asn Ser Ala Phe Lys Ser Pro Asp
    210                 215                 220
Ala Phe Lys Val Ser Leu Pro Leu Arg Thr Asn Tyr Leu Tyr Gly Lys
225                 230                 235                 240
Ile Lys Lys Thr Leu Pro Glu Leu Tyr Ala Phe Thr Ile Cys Leu Trp
                245                 250                 255
Leu Arg Ser Ser Ala Ser Pro Gly Ile Gly Thr Pro Phe Ser Tyr Ala
            260                 265                 270
Val Pro Gly Gln Ala Asn Glu Ile Val Leu Ile Glu Trp Gly Asn Asn
        275                 280                 285
Pro Ile Glu Leu Leu Ile Asn Asp Lys Val Ala Gln Leu Pro Leu Phe
    290                 295                 300
Val Ser Asp Gly Lys Trp His His Ile Cys Ile Thr Trp Thr Thr Arg
305                 310                 315                 320
Asp Gly Met Trp Glu Ala Phe Gln Asp Gly Glu Lys Leu Gly Thr Gly
                325                 330                 335
Glu Asn Leu Ala Pro Trp His Pro Ile Lys Pro Gly Gly Val Leu Ile
            340                 345                 350
Leu Gly Gln Glu Gln Asp Thr Val Gly Gly Arg Phe Asp Ala Thr Gln
        355                 360                 365
Ala Phe Val Gly Glu Leu Ser Gln Phe Asn Ile Trp Asp Arg Val Leu
    370                 375                 380
Arg Ala Gln Glu Ile Ile Asn Ile Ala Asn Cys Ser Thr Asn Met Pro
385                 390                 395                 400
```

```
-continued

Gly Asn Ile Ile Pro Trp Val Asp Asn Asn Val Asp Val Phe Gly Gly
            405             410                 415

Ala Ser Lys Trp Pro Val Glu Thr Cys Glu Glu Arg Leu Leu Asp Leu
            420             425                 430
```

METHOD FOR IDENTIFYING COMPOUNDS WHICH AFFECT IONOTROPIC GLUTAMATE RECEPTOR AGGREGATION

This is a continuation of U.S. patent application Ser. No. 09/328,710 filed Jun. 9, 1999, now abandoned, all of which is hereby incorporated by reference in the disclosure of this application.

STATEMENT AS TO FEDERALLY SPONSORED RESEARCH

This invention was made with Government support under Grant No. K08NS01652, R01NS36715, R01MH53608, and K02MHO1152, awarded by the National Institutes of Health. The government may have certain rights in the invention.

FIELD OF THE INVENTION

The present invention relates generally to molecules involved in synaptogenesis, and more specifically to the role of Narp in the formation of synapses and the clustering of receptors in synapses.

BACKGROUND OF THE INVENTION

The mature central nervous system exhibits the capacity to alter cellular interactions as a function of the activity of specific neuronal circuits. This capacity is believed to underlie learning and memory storage, age-related memory loss, tolerance to and dependence on drugs of abuse, recovery from brain injury, epilepsy as well as aspects of postnatal development of the brain (Schatz, C., Neuron, 5:745, 1990). Currently, the role of activity-dependent synaptic plasticity is best understood in the context of learning and memory. Cellular mechanisms underlying activity-dependent plasticity are known to be initiated by rapid, transmitter-induced changes in membrane conductance properties and activation of intracellular signaling pathways (Bliss and Collingridge, Nature, 361:31, 1993). Several lines of evidence also indicate a role for rapid synthesis of mRNA and protein in long-term neuroplasticity. For example, classical studies of learning and memory demonstrate a requirement for protein synthesis in a long-term, but not short-term memory (Flexner, et al., Science, 141:57, 1963; Agranoff, B., Basic Neurochemistry, 3rd Edition, 1981; Davis and Squire, Physiol. Bull., 96:518, 1984), and long-term enhancement of synaptic connectivity, studied in cultured invertebrate neurons (Montarolo, et al., Science, 234:1249, 1986; Bailey, et al., Neuron, 9:749, 1992) or in the rodent hippocampus (Frey, et al., Science, 260:1661, 1993; Nguyen, et al., Science, 265:1004, 1194), is blocked by inhibitors of either RNA or protein synthesis. Importantly, inhibitors of macromolecular synthesis are most effective when administered during a brief time window surrounding the conditioning stimulus indicating a special requirement for molecules that are rapidly induced (Goelet, et al., Nature, 322:419, 1986).

Immediate early genes (IEGs) are rapidly induced in neurons by neurotransmitter stimulation and synaptic activity and are hypothesized to be part of the macromolecular response required for long-term plasticity (Goelet, et al., supra; Sheng and Greenberg, Neuron, 4:477, 1990; Silva and Giese, Neurobiology, 4:413, 1994). To identify cellular mechanisms that may contribute to long-term plasticity in the vertebrate brain, differential cloning techniques have been used to identify genes that are rapidly induced by depolarizing stimuli (Nedivi, et al., Nature, 363:713, 1993; Qian, et al., Nature, 361:453, 1993; Yamagata, et al., Neuron, 11:371, 1993; Yamagata, et al., Learning and Memory 1:140, 1994; Yamagata, et al., Journal of Biological Chemistry, 269:16333, 1994; Andreasson and Worley, Neuroscience, 69:781, 1995; Lyford, et al., Neuron, 14:433, 1995). In contrast to the earlier focus on transcription factors, many of the newly characterized IEGs represent molecules that can directly modify the function of cells and include growth factors (Nedivi, et al., supra; Andreasson and Worley, supra), secreted enzymes that can modify the extracellular matrix, such as tissue plasminogen activator (Qian, et al., supra), enzymes involved in intracellular signaling, such as prostaglandin synthase (Yamagata, et al., supra), and a novel homolog of H-Ras, termed Rheb (Yamagata, et al., supra), as well as a novel cytoskeleton-associated protein, termed Arc (Lyford, et al., supra). The remarkable functional diversity of this set of rapid response genes is representative of the repertoire of cellular mechanisms that are likely to contribute to activity-dependent neuronal plasticity.

The identification of molecules regulating the aggregation of neurotransmitter receptors at synapses is central to understanding the mechanisms of neural development, synaptic plasticity and learning. The most well characterized model for the synaptic aggregation of ionotropic receptors is the neuromuscular junction. Early work showed that contact between the axon of a motor neuron and the surface of a myotube rapidly triggers the accumulation of preexisting surface acetylcholine receptors (Anderson and Cohen, J. Physiol. 268:757–773, 1977; Frank and Fischbach, J. Cell. Biol. 83:143–158, 1979). Subsequent work has shown that agrin, a complex glycoprotein secreted by the presynaptic terminal, activates a postsynaptic signal transduction cascade (reviewed by Colledge and Froehner, Curr. Opin. Neurobiol. 8:357–63, 1998), that leads to receptor clustering by the membrane associated protein rapsyn.

In the central nervous system, ionotropic glutamate receptors are the major excitatory neurotransmitter receptors and are divided into three broad classes, termed AMPA, NMDA and kainate type receptors, on the basis of molecular and pharmacological criteria (Hollmann, M., and Heinemann, S., Ann. Rev. Neurosci. 17:31–108, 1994). The predominant charge carrier during routine fast excitatory synaptic transmission is the AMPA type receptor, while NMDA receptors contribute a significant calcium current, which is thought to modulate signal transduction pathways. Functional AMPA receptors are multimeric complexes of the homologous subunits GluR1–4 (Rosenmund et al., Science 280:1596–9, 1998; Mano and Teichberg, Neuroreport 9: 327–31 1998) which share about 60% to 70% homology at the amino acid level (Keinanen et al., Science 249:556–60, 1990). A variety of studies have shown that glutamate receptors are highly concentrated in neurons at excitatory synapses on dendritic spines and shafts.

Significant advances in the identification of molecules involved in excitatory synapse formation have recently occurred using genetic and biochemical techniques. A family of cytoplasmic proteins containing protein—protein interaction motifs, called PDZ domains, have been implicated in the clustering of both NMDA and AMPA receptors at synapses (O'Brien et al., Curr. Opin. Neurobiol. 8:364–9 1998). These PDZ domain containing proteins are thought to intracellularly cross link receptors and couple them to the cytoskeleton. The PSD-95 family of proteins contain three PDZ domains, which directly interact with the C-termini of NMDA receptor subunits and may be important in NMDA receptor clustering (Komau et al., *Science* 22:1737–40, 1995). Similarly, the neuronal proteins GRIP (Dong et al., *Nature* 386:279–84, 1997), ABP (Srivastava et al., *Neuron* 21:581–91, 1998), and Pick1 (Xia et al., *Neuron* 22:179–187, 1998), each of which contains one or more PDZ domains, interact with the C-terminus of AMPA receptors and may be important in receptor targeting (Dong et al., supra). The extracellular factors that facilitate the formation of excitatory synapses in the central nervous system have not been identified.

An additional level of complexity in the formation of central excitatory synapses stems from the fact that two populations of neurons exist (termed spiny and aspiny) which receive excitatory input in mutually exclusive patterns (Sloper and Powell, 1979; Harris and Kater, 1994). Spiny neurons, such as hippocampal pyramidal neurons receive more than 90% of their excitatory input onto dendritic spines, while shaft synapses on these neurons are largely inhibitory. Aspiny neurons such as hippocampal interneurons and most spinal neurons receive both excitatory and inhibitory synapses on their dendritic shafts. Emerging evidence indicates that excitatory synapses on spines and shafts have different structural and functional properties which may imply different molecular mechanisms in their formation and maintenance (O'Brien et al., *J. Neurosci.* 17:7339–50, 1997; Rao et al., *J. Neurosci.* 18:1217–29, 1998, amongst others).

SUMMARY OF THE INVENTION

Narp was originally identified using a subtractive cloning strategy from stimulated hippocampus (see U.S. Pat. No. 5,767,252, incorporated by reference). The present invention shows that Narp plays a role in synaptogenesis and in the clustering of AMPA receptors. It therefore follows that other members of the long pentraxin family may play a role in synaptogenesis and in the clustering of AMPA receptors. The present invention is thus directed to long pentraxins in general and Narp is discussed for purposes of an exemplary long pentraxin of the invention. It should be understood that the methods of the invention are useful for all long pentraxins, which are known in the art as a family of proteins that are found in the brain and share a core pentraxin domain. Narp and NP-1 additionally include an extended N-terminus that appears to function in clustering. NP-1 is secreted and forms clusters on the surface of expressing cells, similar to observations with Narp.

A method is provided for identifying a compound which affects the formation of AMPA receptors into aggregates. The method includes incubating the compound and a pre-synaptic cell expressing Long pentraxin (e.g., Narp) under conditions sufficient to allow the compound to interact with the cell, and determining the effect of the compound on the formation of AMPA receptors into aggregates in the pre-synaptic cell or in a post-synaptic cell synapsing with the pre-synaptic cell. The formation of AMPA receptors into aggregates of the pre-synaptic cell contacted with the compound, or in the post-synaptic cell is compared with the formation of AMPA receptors into aggregates in a pre-synaptic cell not contacted with the compound or a post-synaptic cell synapsing with the pre-synaptic cell not contacted with the compound.

A method is provided for identifying a compound which affects the formation of synaptic connections. The method includes incubating the compound and a cell expressing Long pentraxin (e.g., Narp) under conditions sufficient to allow the compound to interact with the cell and determining the effect of the compound on the formation of synaptic connections. The synaptic connections of the cell contacted with the compound is compared with the synaptic connections of a cell not contacted with the compound.

A method is provided for identifying a compound that modulates immediate early gene expression. The method includes contacting a test compound with a sample comprising a nucleic acid encoding Long pentraxin (e.g., Narp) and determining whether the test compound effects the expression of the immediate early gene nucleic acid, wherein the presence of an effect indicates that the test compound modulates immediate early gene expression.

A method is provided for increasing the number of excitory synapses of a neuron, including introducing into the neuron a polynucleotide sequence encoding a Long pentraxin (e.g., Narp) operatively linked to a promoter, thereby increasing the number of excitory synapses of the neuron.

A method is provided for increasing the number of excitory synapses of a neuron, including introducing into the neuron a Long pentraxin (e.g., Narp) polypeptide, thereby increasing the number of excitory synapses of the neuron.

A method is provided for treating a subject with a disorder associated with a decrease in a function or expression of Long pentraxin (e.g., Narp), including administering to the subject a therapeutically effective amount of a compound that augments Long pentraxin (e.g., Narp) function or expression.

A method is provided for treating a subject with a disorder associated with an increase in a function or expression of Long pentraxin (e.g., Narp), including administering to the subject a therapeutically effective of a compound that inhibits Long pentraxin (e.g., Narp) function or expression.

A method is provided for treating a patient having or at risk of having a disorder associated with decreased Long pentraxin (e.g., Narp) expression. The method includes introducing into a cell of a patient having a disorder associated with decreased Long pentraxin (e.g., Narp) expression or function a polynucleotide sequence encoding a Long pentraxin (e-g., Narp) polypeptide operatively linked to a promoter, thereby augmenting a function of Long pentraxin (e.g., Narp).

A method is provided for treating a subject having a deficiency in a neuron's immediate early gene responsiveness to a stimulus. The method includes administering a nucleic acid encoding a Long pentraxin (e.g., Narp) polypeptide to said subject, wherein the administration results in amelioration of the deficiency.

A pharmaceutical composition is provided including a therapeutically effective mount of an expression vector including a nucleic acid encoding a Long pentraxin (e.g., Narp) polypeptide or a conservative variant thereof and a pharmaceutically acceptable carrier.

BRIEF DESCRIPTION OF THE DRAWINGS

Figure 1A:
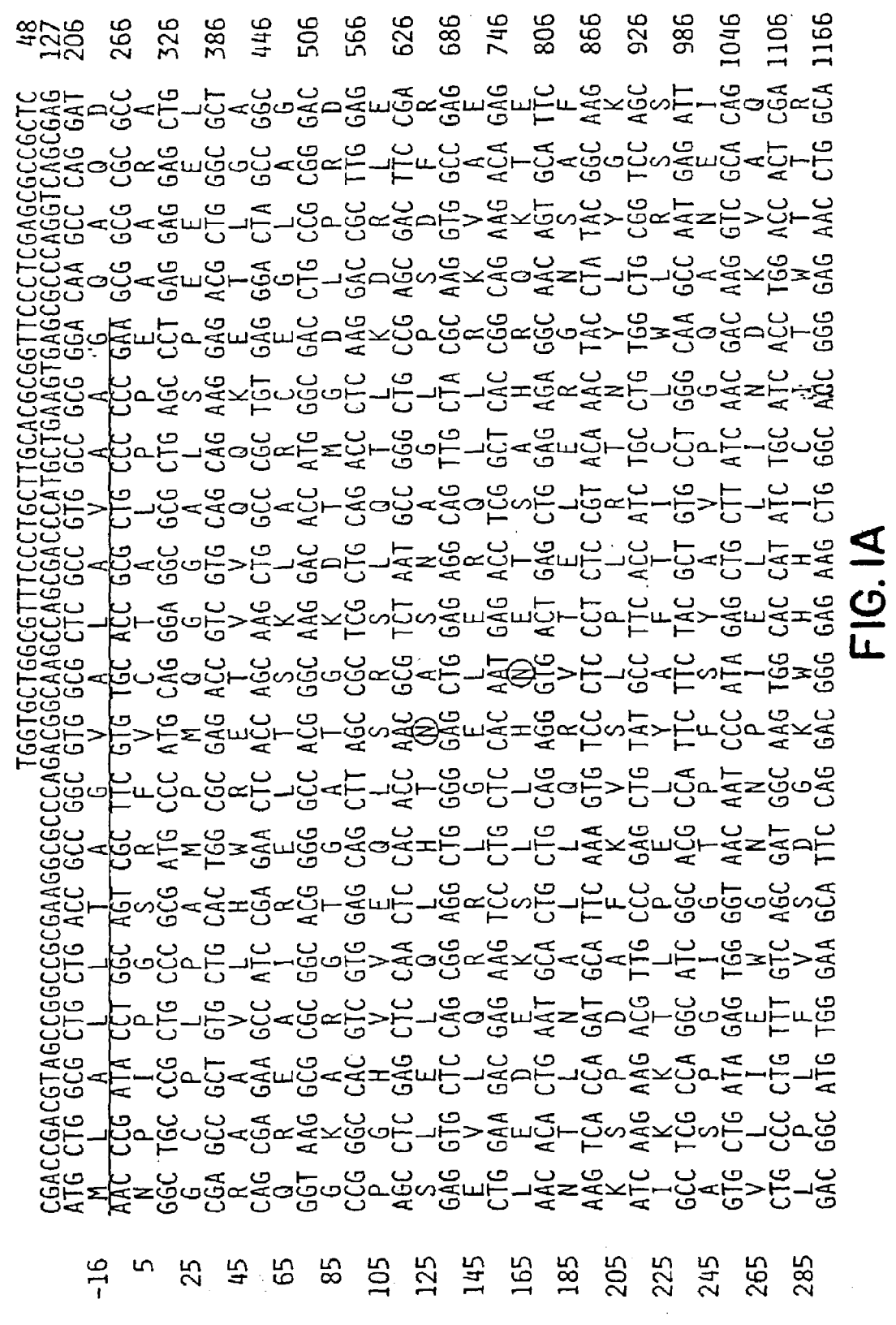
Figure 1B:
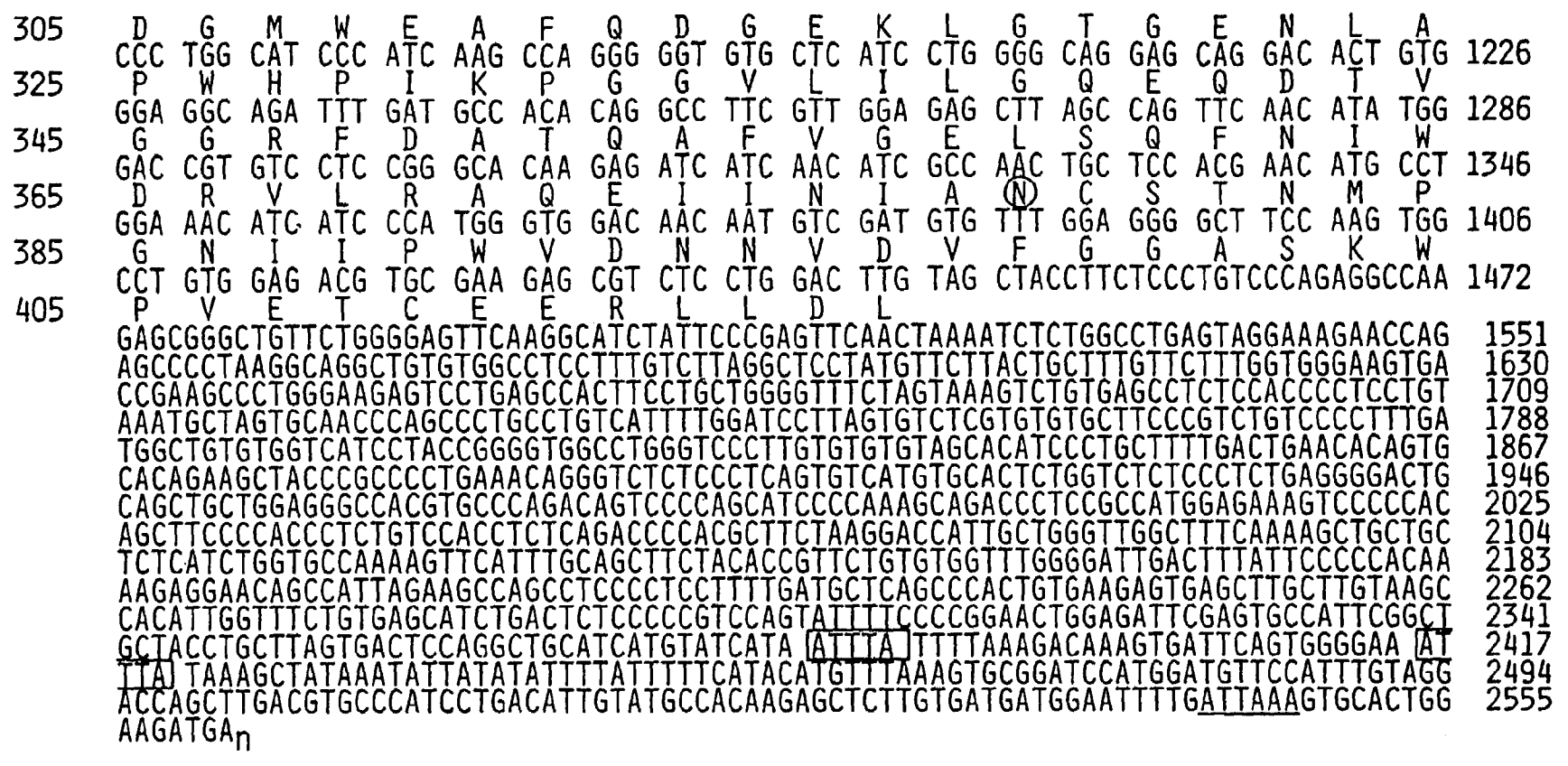

FIG. 1 shows the nucleotide sequence of Narp cDNA (SEQ ID NO: 1) and its predicted amino acid sequence (SEQ ID NO:2). The last nucleotide of each line is numbered to the right. The translated protein sequence is shown below corresponding nucleotide sequence and is numbered on the left side. The putative signal peptide of 16 amino acids is underlined. A dot indicates the predicted first amino acid of the mature protein. Putative glycosylation sites are circled. Two putative ATTTA mRNA instability motifs are present in the 3' untranslated region and are boxed. The putative polyadenylation signal (ATTAAA) is underlined (sequence as shown in: Tsui et al., *J. Neurosci.* 16:2463–78, 1996, herein incorporated by reference.

DETAILED DESCRIPTION OF THE INVENTION

Narp was originally identified using a subtractive cloning strategy from stimulated hippocampus (Tsui et al., *J. Neurosci.* 16: 2463–78, 1996, herein incorporated by reference) and was identified as a member of the newly recognized subfamily of "long pentraxins" that includes neuronal pentraxin 1 and 2 (Narp), which are found in the brain (Schlimgen et al., *Neuron* 14:519–26, 1995), TSG-14 (Lee et al., *J. Immunol.* 150:1804–12, 1993); a TNF inducible acute phase reactant; and Apexin (Reid and Blobel, *J. Biol. Chem.* 269:32615–20, 1994; Rothstein et al., *Neuron* 13:713–25, 1994), which is localized to the acrosome of mature sperm. These molecules are similar in structure in that they possess a C-terminal pentraxin domain and a ~200 aa unique N-terminus whose function is unknown (Goodman et al., *Cytokine Growth Factor Rev.* 7:191–202, 1996). The pentraxin domain on Narp is similar to the mammalian proteins C-reactive protein (CRP), serum amyloid protein (SAP), as well as highly conserved homologs from species as distant as *Limulus*. (Tsui et al., 1996, supra). Pentraxins are secreted proteins that self multimerize to form pentamers and may further dimerize to form decamers, (Gewurz et al., *Curr. Opin. Immunol.* 7:54–64, 1995). A crystal structure of SAP showed that the pentraxin sugar binding motif is remarkably homologous in secondary and tertiary structure to the plant lectin concanavalin A (Emsley et al., *Nature* 367, 338–45, 1994), a feature that is conserved in Narp (Tsui et al., 1996, supra). The physiological roles of pentraxins have remained obscure, although CRP has been postulated to play a role in non-antibody mediated immune responses by binding and aggregating bacteria and other pathogens (Siegel et al., *J. Exp. Med.* 140:63147, 1974; Siegel et al., *J. Exp. Med.* 142: 709–2 1 1975).

An exemplary polynucleotide encoding Narp is set forth as SEQ ID NO: 1. The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. A polynucleotide encoding Narp includes "degenerate variants," sequences that are degenerate as a result of the genetic code. There are 20 natural amino acids, most of which are specified by more than one codon. Therefore, all degenerate nucleotide sequences are included in the invention as long as the amino acid sequence of a polypeptide encoded by the nucleotide sequence of SEQ ID NO: 1 is functionally unchanged.

A polynucleotide encoding Narp includes a polynucleotide encoding functional Narp polypeptides as well as functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of Narp polypeptide," refers to all fragments of a Narp that retain a Narp activity, e.g., the ability to recruit AMPA receptors into aggregates or to facilitate the formation of new excitatory synapses. Biologically functional fragments, for example, can vary in size from a polypeptide fragment as small as an epitope capable of binding an antibody molecule to a large polypeptide capable of participating in the characteristic induction or programming of phenotypic changes within a cell.

A functional Narp polypeptide includes the polypeptide as set forth in SEQ ID NO:2 and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Excitory amino acid receptors (EAA receptors) are the major class of excitatory neurotransmitter receptors in the central nervous system. "EAA receptors" are membrane spanning proteins that mediate the stimulatory actions of glutamate and possibly other endogenous acidic amino acids. EAA are crucial for fast excitatory neurotransmission and they have been implicated in a variety of diseases including Alzheimer's disease and epilepsy. In addition, EAA are integral to the processes of long-term potentiation, one of the synaptic mechanisms underlying learning and memory. There are three main subtypes of EAA receptors: (1) the metabotropic or trans ACPD receptors, (2) the ionotropic NMDA receptors, and (3) the non-NMDA receptors, which include the AMPA receptors.

Ionotropic glutamate receptors are generally divided into two classes: the NMDA and non-NMDA receptors. Both classes of receptors are linked to integral cation channels and share some amino acid sequence homology. Seven non-NMDA glutamate receptor subunits have been cloned thus far. GluR1–4 are termed AMPA (α-amino-3-hydroxy-5-methylisoxazole-4-propionic acid) receptors because AMPA preferentially activates receptors composed of these subunits, while GluR5–7 are termed kainate receptors as these are preferentially sensitive to kainic acid. Thus, an "AMPA receptor" is a non-NMDA receptor that can be activated by AMPA. AMPA receptors include the GluR1–4 family, which form homo-oligomeric and hetero-oligomeric complexes which display different current-voltage relations and $Ca^{2+}$ permeability. Polypeptides encoded by GluR1–4 nucleic acid sequences can form functional ligand-gated ion channels. Therefore, an AMPA receptor includes a receptor having a GluR1, GluR2, GluR3 or GluR4 subunit.

Activation of an AMPA receptor results in the opening of associated $Na^+$ channels and the generation of excitatory postsynaptic potentials. An "excitatory postsynaptic potential" or "EPSP" is a transient change in the membrane potential in a postsynaptic neuron caused by the binding of an excitatory neurotransmitter released by the corresponding presynaptic neuron to postsynaptic receptors. In general, the membrane potential changes in a depolarizing direction, although this is not always the case. The depolarization, during which membrane potential becomes more positive, reflects an increased excitability of the cell as the membrane potential is brought closer to the threshold for the generation of an action potential. An EPSP can be a "fast EPSP," with an amplitude on the order of millivolts, with a latency of tens of milliseconds, and a duration of hundreds of milliseconds. However, some cells exhibit "slow EPSPs" with a long latency (approximately 0.5 seconds or more), and a prolonged time course.

Under certain conditions, AMPA receptors are known to form aggregates. An "aggregate" is a cluster of AMPA receptors. Methods for demonstrating the formation of aggregates are well known in the art (e.g., immunohistochemical methods). (See examples section for additionally methodology.) A method is provided for identifying a compound which affects the formation of AMPA receptors into aggregates. The method includes incubating the compound and a cell expressing Narp under conditions sufficient to allow the compound to interact with the cell. The cell can be a pre-synaptic cell or a post-synaptic cell. The pre- or post-synaptic cell can be any cell of interest. The effect of the compound on the formation of AMPA receptors into aggregates is then determined. The effect can be determined directly in the pre-synaptic cell, or the effect can be determined in a post-synaptic cell synapsing with the pre-synaptic cell. The formation of AMPA receptors into aggregates of the cell is then compared with the formation of AMPA receptors into aggregates in a control. Suitable controls include, but are not limited to, the formation of AMPA receptors into aggregates in a pre-synaptic cell not contacted with the compound or a post-synaptic cell synapsing with the pre-synaptic cell not contacted with the compound.

The compounds which affect the aggregation of AMPA receptors can include peptides, peptidomimetics, polypeptides, pharmaceuticals, and chemical compounds and biological agents. Antibodies, neurotropic agents, and anti-epileptic compounds can also be tested using the method of the invention.

"Incubating" includes conditions which allow contact between the test agent and the cell of interest. "Contacting" includes in solution or in solid phase. Candidate compounds that affect Narp include chemical compounds. One class is organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

The test agent may also be a combinatorial library for screening a plurality of compounds. Compounds such as peptides identified in the method of the invention can be further cloned, sequenced, and the like, either in solution of after binding to a solid support, by any method usually applied to the isolation of a specific DNA sequence Molecular techniques for DNA analysis (Landegren et al., *Science* 242:229–237, 1988) and cloning have been reviewed (Sambrook et al. *Molecular Cloning: a Laboratory Manual*, 2nd ed.; Cold Spring Harbor Laboratory Press, Plainview, N.Y., 1998, herein incorporated by reference).

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including, but not limited to: peptides, saccharides, fatty acids, steroids, purines, pyrimidines, derivatives, structural analogs or combinations thereof.

A compound can affect AMPA receptor aggregation by either stimulating or inhibiting the receptor aggregation. A compound "inhibits" AMPA receptor aggregation level of aggregation of AMPA receptors is decreased as compared with the level in the absence of the test compound. A compound "stimulates" AMPA receptor aggregation if the level of AMPA receptor aggregation is increased as compared to a control in the absence of the test compound.

A variety of other agents may be included in the screening assay. These include agents like salts, neutral proteins, e.g., albumin, detergents, etc. that are used to facilitate optimal protein—protein binding and/or reduce nonspecific or background interactions. Reagents that improve the efficiency of the assay, such as protease inhibitors, nuclease inhibitors, antimicrobial agents, etc., may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 hours will be sufficient.

The sample can be any sample of interest. The sample may be a cell sample or a membrane sample prepared from a cell sample. Suitable cells include any host cells containing Narp. The cells can be primary cells or cells of a cell line. In one embodiment, the sample is a primary cell, such as a neuronal cell, that expresses Narp. In another embodiment, the cell is a cell line that expresses Narp. Specific, non-limiting examples of cells suitable for use with the method of the invention are cultured hippocampal neurons or spinal neurons. Methods of culturing neuronal cell suitable for use in the method of the invention are known to one of skill in the art (see O'Brien et al., *Neuron* 21:1067–98, 1998; O'Brien et al., *Curr. Opin. Neurobiol.* 8:364–9, 1998; O'Brien et al., *J. Neurosci.* 17:7339–50, 1997; Mammen et al., *J. Neurosci.* 17: 7351–8, 1997; Liao et al., *Nature Neurosci.* 2:37–43, 1999, all herein incorporated by reference).

In yet another embodiment, the sample is a host cell transfected with a nucleic acid encoding Narp. The nucleic acid encoding Narp can be included in a nucleic acid encoding a fusion protein, wherein the nucleic acid encoding Narp is linked to a nucleic acid encoding another polypeptide. The fusion protein can be a Narp polypeptide linked to a readily detectible polypeptide. A "detectible polypeptide" is any polypeptide that can be readily identified using methods well known to one of skill in the art. In one embodiment, the detectible polypeptide can be an antigen which can be specifically bound by an antibody of interest (e.g., myc antigen and an anti-myc antibody). In another embodiment, the detectible polypeptide can catalyze an enzymatic reaction (e.g., lacZ). In yet another embodiment, the detectible polypeptide can be detected by its physical parameters (e.g., fluorescence when excited with light of a specific wavelength) or spatial parameters.

DNA sequences encoding Narp can be expressed in vitro by transfer of nucleic acid into a suitable host cell. "Host cells" are cells in which a vector can be propagated and its nucleic acid expressed. In a preferred embodiment, the host cell is eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the Narp polynucleotide sequences may be inserted into an expression vector. The term "expression vector" refers to a plasmid, virus or other vehicle known in the art that has been manipulated by insertion or incorporation of the Narp genetic sequences. Polynucleotide sequence which encode Narp can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, as start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., 1987, *Methods in Enzymology* 153:516–544). For example, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the polynucleotide encoding Narp may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. A specific, non-limiting example of a vectors suitable for use in the present invention include, but are not limited to the pMSXND expression vector for expression in mammalian cells (Lee and Nathans, 1988, *J. Biol. Chem.* 263:3521), amongst others. The DNA segment can be present in the vector operably linked to regulatory elements, for example, a promoter (e.g., T7, metallothionein I, neurofilament, or polyhedrin promoters).

In yeast, a number of vectors containing constitutive or inducible promoters may be used. For a review see, *Current Protocols in Molecular Biology*, Vol. 2, 1988, Ed. Ausubel et al., Greene Publish. Assoc. & Wiley Interscience, Ch. 13; Grant et al., 1987, "Expression and Secretion Vectors for Yeast," in *Methods in Enzymology*, Eds. Wu & Grossman, 31987, Acad. Press, N.Y., Vol. 153, pp. 516–544; Glover, 1986, *DNA Cloning*, Vol. II, IRL Press, Wash., D.C., Ch. 3; and Bitter, 1987, "Heterologous Gene Expression in Yeast," Methods in Enzymology, Eds. Berger & Kimmel, Acad. Press, N.Y., Vol. 152, pp. 673–684; and *The Molecular Biology of the Yeast Saccharomyces*, 1982, Eds. Strathem et al., Cold Spring Harbor Press, Vols. I and II. A constitutive yeast promoter such as ADH or LEU2 or an inducible promoter such as GAL may be used ("Cloning in Yeast," Ch. 3, R. Rothstein In: *DNA Cloning* Vol. 11, A Practical Approach, Ed. D. M. Glover, 1986, IRL Press, Wash., D.C.). Alternatively, vectors may be used which promote integration of foreign nucleic acid sequences into the yeast chromosome. Yeast may be used to search for molecules that disrupt interaction between Narp molecules or Narp and AMPA receptor, for example, by co-expressing Narp and AMPA receptor or fragments thereof, that interact.

Mammalian expression systems which utilize recombinant viruses or viral elements to direct expression may be engineered. For example, when using adenovirus expression vectors, the Narp coding sequence may be ligated to an adenovirus transcription/translation control complex, e.g., the late promoter and tripartite leader sequence. Alternatively, the vaccinia virus 7.5K promoter may be used (e.g., see, Maced. et al., 1982, *Proc. Natl. Acad. Sc. USA* 79:7415–7419; Maced. et al., 1984, *J. Biol.* 49:857–864; Panniculi et al., 1982, *Proc. Natl. Acad. Sc. USA* 79:4927–4931). Of particular interest are vectors based on bovine papilloma virus which have the ability to replicate as extrachromosomal elements (Salver, et al., 1981, *Mol. Cell. Biol.* 1:486). Shortly after entry of this nucleic acid into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the Narp gene in host cells (Cone & Mulligan, 1984, *Proc. Natl. Acad. Sc. USA* 81:6349–6353). High level expression may also be achieved using inducible promoters, including, but not limited to, the metallothionein I.A. promoter and heat shock promoters.

Hosts can include yeast and mammalian organisms. Methods of expressing DNA sequences having eukaryotic or viral sequences in eukaryotes are well known in the art. In addition, prokaryotic cells, such as bacterial cells can be used for the production of Narp protein of use with the subject invention. Biologically functional viral and plasmid DNA vectors capable of expression and replication in a host are known in the art. Such vectors are used to incorporate nucleic acid sequences of the use with the invention.

For long-term, high-yield production of recombinant proteins, stable expression is preferred. Rather than using expression vectors which contain viral origins of replication, host cells can be transformed with Narp cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign nucleic acid, engineered cells may be allowed to grow for 1–2 days in an enriched media, and then are switched to a selective media. A number of selection systems may be used, including, but not limited to the herpes simplex virus thymidine kinase gene (Wigler, et al., 1977, *Cell* 11:223), hypoxanthine-guanine phosphoribosyltransferase gene (Szybalska & Szybalski, 1962, *Proc. Natl. Acad. Sci. USA* 48:2026), and the adenine phosphoribosyltransferase [Lowy, et al., 1980, *Cell* 22:817) genes can be employed in tk-, hgprt or aprt cells respectively. Additionally, antimetabolite resistance can be used as the basis of selection for which confers resistance to methotrexate (Wigler, et al., 1980, *Natl. Acad. Sci. USA* 77:3567; O'Hare, et al., 1981, *Proc. Natl. Acad. Sci. USA* 78: 1527); the gpt gene, which coders resistance to mycophenolic acid (Mulligan & Berg, 1981, *Proc. Natl. Acad. Sci. USA* 78:2072; the neo gene, which confers resistance to the aminoglycoside G-418 (Colberre-Garapin, et al., 1981, *J. Mol. Biol.* 150:1); and the hygro gene, which confers resistance to hygromycin (Santerre, et al., 1984, *Gene* 30:147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA* 85:8047); and ODC (ornithine decarboxylase) which confers resistance to the ornithine decarboxylase inhibitor, 2-(difluoromethyl)-DL-ornithine, DFMO (McConlogue L., 1987, In: *Current Communications in Molecular Biology*, Cold Spring Harbor Laboratory ed.).

By "transformation" is meant a genetic change induce in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which has been introduced, by means of recombinant DNA techniques, a nucleic acid molecule encoding Narp. Transformation of a host cell with recombinant DNA may be carried out by conventional techniques as are well known to those skilled in the art. Where the host is prokaryotic, such as *E. coli*, and is used for the production of Narp polypeptide, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired. Vectors for the transformation of prokaryotic cells are well known to one of skill in the art (see Sambrook et al., supra).

When the host is a eukaryote, such methods of transfection of DNA as calcium phosphate co-precipitates, conventional mechanical procedures such as microinjection, electroporation insertion of a plasmid encased in liposomes, or virus vectors may be used. Eukaryotic cells can also be cotransformed with DNA sequences encoding Narp, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

In another embodiment, a method is provided for identifying a compound which affects the formation of synaptic connections. The method includes incubating the compound and a cell expressing Narp under conditions sufficient to allow the compound to interact with the cell, determining the effect of the compound on the formation of synaptic connections, and comparing the synaptic connections of the cell contacted with the compound with the synaptic connections of a cell not contacted with said compound. A "synaptic connection" or a "synapse" is a specialized junction between two nerve cells or between a nerve and a muscle cell across which signals are transmitted. A synapse can be a chemical synapse or an electrical synapse. A "chemical synapse" is a synapse where the plasma membrane of the axon terminal of the transmitting neuron and that of the receiving cell are separated by a small gap. Chemical neurotransmitters are released from the axon terminal, diffuse across the synapse, and stimulate receptors on the postsynaptic membrane. An "electrical synapse" is a synapse where an electrical signal carried by ions is transmitted from one cell to another by a gap junction. Methods for analyzing and quantitating synaptic connections are well known to one of skill in the art and provided in the Examples as well.

A compound can affect synapse formation by either stimulating or inhibiting the formation of synaptic connections. A compound "inhibits" formation of synaptic connections if the level of formation of synaptic connections is decreased as compared with the level in the absence of the test compound. A compound "stimulates" formation of synaptic connections if the level of formation of synaptic connections is increased as compared to a control in the absence of the test compound.

The sample can be any sample of interest. The sample may be a cell sample or a membrane sample prepared from a cell sample. Suitable cells include any host cells containing Narp. The cells can be primary cells or cells of a cell line that express Narp. In one embodiment, the sample is a primary cell, such as a neuronal cell, that expresses Narp. In another embodiment, the cell is a cell line that expresses Narp. In yet another embodiment, the sample is a host cell transfected with a nucleic acid encoding Narp. The nucleic acid encoding Narp may be including in a nucleic acid encoding a fusion protein, wherein the nucleic acid encoding Narp is linked to a nucleic acid encoding another polypeptide.

A method is also provided for identifying a compound that modulates the expression of an immediate early gene. The method includes contacting a test compound with a sample comprising a nucleic acid encoding Narp; and determining whether the test compound affects the expression of the immediate early gene nucleic acid, wherein the presence of an effect indicates that the test compound modulates immediate early gene expression.

Immediate early genes (IEGs) are rapidly induced in neurons by neurotransmitter stimulation and synaptic activity and are hypothesized to be part of the macromolecular response required for long-term plasticity (Goelet, et al., supra; Sheng and Greenberg, *Neuron*, 4:477, 1990; Silva and Giese, *Neurobiology,* 4:413, 1994). To identify cellular mechanisms that may contribute to long-term plasticity in the vertebrate brain, differential cloning techniques have been used to identify genes that are rapidly induced by depolarizing stimuli (Nedivi, et al., *Nature,* 363:713, 1993; Qian, et al., *Nature,* 361:453, 1993; Yamagata, et al., *Neuron,* 11:371, 1993; Yamagata, et al., *Learning and Memory* 1: 140, 1994; Yamagata, et al., *Journal of Biological Chemistry,* 269:16333, 1994; Andreasson and Worley, *Neuroscience,* 69:781, 1995; Lyford, et al., *Neuron,* 14:433, 1995). In contrast to the earlier focus on transcription factors, many of the newly characterized IEGs represent molecules that can directly modify the function of cells and include growth factors (Nedivi, et al., supra; Andreasson and Worley, supra), secreted enzymes that can modify the extracellular matrix, such as tissue plasminogen activator (Qian, et al., supra), enzymes involved in intracellular signaling, such as prostaglandin synthase (Yamagata, et al., supra), and a novel homolog of H-Ras, termed Rheb (Yamagata, et al., supra), as well as a novel cytoskeleton-associated protein, termed Arc (Lyford, et al., supra). The remarkable functional diversity of this set of rapid response genes is representative of the repertoire of cellular mechanisms that are likely to contribute to activity-dependent neuronal plasticity.

An "immediate early gene" or an "IEG" is a gene whose expression is rapidly increased immediately following a stimulus. For example, genes expressed by neurons that exhibit a rapid increase in expression immediately following neuronal stimulation are neuronal IEGs. Such neuronal IEGs have been found to encode a wide variety of polypeptides including transcription factors, cytoskeletal polypeptides, growth factors, and metabolic enzymes as well as polypeptides involved in signal transduction. The identification of neuronal IEGs and the polypeptides they encode provides important information about the function of neurons in, for example, learning, memory, synaptic transmission, tolerance, and neuronal plasticity.

In another embodiment, a method is provided for increasing the number of excitatory synapses of a neuron, comprising introducing into the neuron a polynucleotide sequence encoding a Narp, operatively linked to a promoter, thereby increasing the number of excitory synapses of the neuron. The polynucleotide sequence encoding Narp may be introduced into the neuron in vitro. Alternatively, the polynucleotide sequence encoding Narp can be introduced into the neuron in vivo. A method is also provided for increasing the number of excitory synapses of a neuron, comprising introducing into the neuron a Narp polypeptide, thereby increasing the number of excitory synapses of the neuron.

A method is further provided for treating a subject with a disorder associated with a decrease in a function or expression of Narp, comprising administering to the subject a therapeutically effective amount of a compound that augments Narp function or expression. In yet another embodiment, a method is provided for treating a subject with a disorder associated with a decrease in function or expression of Narp, comprising administering to the subject a therapeutically effective amount of a polynucleotide encoding Narp.

Essentially, any disorder which is etiologically linked to increased expression of Narp could be considered susceptible to treatment with an agent that inhibits Narp expression or activity. Any disorder which is etiologically linked to decreased expression of Narp could be considered susceptible to treatment with an agent that stimulates Narp expression or activity. The disorder may be a neuronal cell disorder. Examples of neuronal cell disorders include but are not limited to Alzheimer's disease, Parkinson's disease, stroke, epilepsy, neurodegenerative disease, Huntington's disease, and brain or spinal cord injury/damage, including ischemic injury.

Detection of altered (decreased or increased) levels of Narp expression can be accomplished by hybridization of nucleic acids isolated from a cell of interest with a Narp polynucleotide of the invention. Analysis, such as Northern Blot analysis, are utilized to quantitate expression of Narp, such as to measure Narp transcripts. Other standard nucleic acid detection techniques will be known to those of skill in the art. Detection of altered levels of Narp can also accomplished using assays designed to detect Narp polypeptide. For example, antibodies that specifically bind Narp polypeptide can be utilized. Analyses, such as radioimmune assay or immunohistochemistry, are then used to measure Narp, such as to measure protein concentration qualitatively or quantitatively.

Treatment can include modulation of Narp gene expression or Narp activity by administration of a therapeutically effective amount of a compound that modulates Narp. The term "modulate" envisions the suppression of Narp activity or expression when Narp is overexpressed or has an increased activity as compared to a control. The term "modulate" also includes the augmentation of the expression of Narp when it is underexpressed or has a decreased activity as compared to a control. The term "compound" as used herein describes any molecule, e.g., protein, nucleic acid, or pharmaceutical, with the capability of altering the expression of Narp polynucleotide or activity of Narp polypeptide.

Candidate agents include nucleic acids encoding a Narp, or that interfere with expression of Narp, such as an antisense nucleic acid. Candidate agents also encompass numerous chemical classes wherein the agent modulates Narp expression or activity.

Where a disorder is associated with the increased expression of Narp, nucleic acid sequences that interfere with the expression of Narp can be used. In this manner, the clustering of AMPA receptors, or the formation of excitory synapses, can be inhibited. This approach also utilizes, for example, antisense nucleic acid, ribozymes, or triplex agents to block transcription or translation of Narp mRNA, either by masking that mRNA with an antisense nucleic acid or triplex agent, or by cleaving it with a ribozyme in disorders associated with increased Narp. Alternatively, a dominant negative form of Narp polypeptide could be administered. In one embodiment an agent which decreases Narp expression can be administered to a subject having a disorder associated with increased number of synapses. Such disorders are associated with central or peripheral nervous tissue. In one specific, non-limiting example the disorder is epilepsy. In one specific non-limiting example the disorder is a stroke.

When Narp is overexpressed, candidate agents include antisense nucleic acid sequences. Antisense nucleic acids are DNA or RNA molecules that are complementary to at least a portion of a specific mRNA molecule (Weintraub, 1990, *Scientific American,* 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, 1988, *Anat. Biochem.,* 172:289).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, *Antisense Res. and Dev.*, 1(3):227; Helene, C., 1991, *Anticancer Drug Design*, 6(6):569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, *J. Amer. Med. Assn.*, 260:3030). A major advantage of this approach is that, because they are sequence-specific, only mRNAs with particular sequences are inactivated.

There are two basic types of ribozymes namely, tetrahymena-type (Hasselhoff, 1988, *Nature*, 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Where a disorder is associated with the decreased expression of Narp, nucleic acid sequences that encode Narp can be used. An agent which modulates Narp expression includes a polynucleotide encoding the polypeptide of SEQ ID NO:2, or a conservative variant thereof. Alternatively, an agent of use with the subject invention includes agents that increase the expression of a polynucleotide encoding Narp or an agent that increases the activity of Narp polypeptide. In one embodiment, an agent which increases Narp expression or function is administered to a subject having a disorder associated with a decreased number of synapses.

The method of treating a subject with a neuronal disorder associated with a decreased expression of Narp includes intracerebral grafting of neurons expressing Narp to the region of the CNS having the disorder. Where necessary, the neuron can be genetically engineered to contain a second exogenous gene. The disorder may be from either disease or trauma (injury). Neuronal transplantation, or "grafting" involves transplantation of cells into the central nervous system or into the ventricular cavities or subdurally onto the surface of a host brain. Such methods for grafting will be known to those skilled in the art and are described in *Neural Grafting in the Mammalian CNS*, Bjorklund and Stenevi, eds., (1985), and U.S. Pat. No. 5,082,670 incorporated by reference herein. Procedures include intraparenchymal transplantation, (i.e., within the host brain) achieved by injection or deposition of tissue within the host brain so as to be apposed to the brain parenchyma at the time of transplantation.

Administration of the neurons into selected regions of the recipient subject's brain may be made by drilling a hole and piercing the dura to permit the needle of a microsyringe to be inserted. The neurons can alternatively be injected intrathecally into the spinal cord region. The neuronal preparation permits grafting of neurons to any predetermined site in the brain or spinal cord, and allows multiple grafting simultaneously in several different sites using the same cell suspension and permits mixtures of cells from different anatomical regions. The present invention provides a method for transplanting various neural tissues, by providing previously unavailable neurons in order to grow a sufficient number of cells for in vitro gene transfer followed by in vivo implantation.

The neuron used for treatment of a neuronal disorder associated with decreased function or expression of Narp may optionally contain a second exogenous gene, for example, an oncogene, a gene which encodes a receptor, or a gene which (encodes a ligand, and/or a Narp-encoding polynucleotide. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by a donor neuroblast would be beneficial in a disorder where the subject's neural cell is defective in the production of such a gene product. A neuron genetically modified to secrete a neurotrophic factor, such as nerve growth factor, (NGF), or Narp might be used to prevent degeneration of cholinergic neurons that might otherwise die without treatment. Alternatively, neurons to be grafted into a subject with a disorder of the basal ganglia, such as Parkinson's disease, can be modified to contain an exogenous gene encoding Narp, and/or L-DOPA, the precursor to dopamine. Parkinson's disease is characterized by a loss of dopamine neurons in the substantia-nigra of the midbrain, which have the basal ganglia as their major target organ. Alternatively, neurons derived from substantia-nigra neuronal cells which produce dopamine could be introduced into a Parkinson's patient brain to provide cells which "naturally" produce dopamine.

Other neuronal disorders that may be associated with a decreased expression of Narp, that can be treated by the method of the invention, include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic neurons, or neurons containing an exogenous gene for Narp which would promote synaptogenesis of neurons can be accomplished by the method of the invention, as described. Following a stroke, there is selective loss of cells in the CA1 of the hippocampus as well as cortical cell loss which may underlie cognitive function and memory loss in these patients. Engraftment of neurons expressing Narp, or therapy with nucleic acid sequences encoding Narp, can be used to increase the number of synapses or the clustering of AMPA receptors, in selected regions of the nervous system. The engraftment of neurons may affect learning or memory.

The method of treating a subject with a neuronal disorder also contemplates the grafting of neurons expressing Narp in combination with other therapeutic procedures useful in the treatment of disorders of the CNS. For example, the neurons can be co-administered with agents such as growth factors, gangliosides, antibiotics, neurotransmitters, neurohormones, neurotrophins, toxins, neurite promoting molecules and antimetabolites and precursors of these molecules such as the precursor of dopamine, L-DOPA.

The present invention also provides gene therapy for the treatment of disorders which are associated with Narp. Such therapy would achieve its therapeutic effect by introduction of a therapeutic polynucleotide into cells in vivo having the disorder or introducing the therapeutic polynucleotide into cells ex vivo and then reintroducing the cells into the subject. The "therapeutic polynucleotide" may be polynucleotide sequences encoding Narp, or antisense polynucleotide specific for Narp, designed to treat a Narp-associated disorder. Polynucleotides encoding dominant negative forms of Narp polypeptides or antisense polynucleotides specific for Narp are also included.

Delivery of the therapeutic polynucleotide can be achieved using a recombinant expression vector such as a chimeric virus or a colloidal dispersion system. Especially preferred for therapeutic delivery of antisense sequences, or Narp polynucleotides, is the use of viral vectors or the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), Rous Sarcoma Virus (RSV) or lentiviral vectors (e.g., derived from HIV or FIV, for example). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a Narp sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the Narp polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 µm can encapsulate a substantial percentage of an aqueous buffer containing large macromolecules. RNA, DNA and intact virions can be encapsulated within the aqueous interior and be delivered to cells in a biologically active form (Fraley et al., 1981, *Trends Biochem. Sci.*, 6:77). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., 1988, *Biotechniques,* 6:682).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidiylserine, phosphatidylethanolamine, sphingo-lipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

This invention involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro) capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, 1990, *Science*, 249:1527–1533, which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., 1990, Goodman And Gilman's: *The Pharmacological Bases of Therapeutics*, 8th ed., Pergamon Press; and *Remington's Pharmaceutical Sciences*, 1990, 17th ed., Mack Publishing Co., Easton, Pa., each of which is herein incorporated by reference.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLES

Example 1

NARP is Enriched at Excitatory Synapses in a Subpopulation of Neurons from Hippocampus and Spinal Cord To study Narp protein, a rabbit polyclonal antibody was generated against a full length GST fusion protein of Narp. On western blot, this antibody recognized a single broad protein band centered at 56 kDa in rat brain, similar to the size of recombinant Narp expressed in detergent extracts of transfected HEK-293 cells. Narp protein was also detected as a similar sized triplet in rat testes, but not in other peripheral tissues. This restricted distribution of Narp protein parallels the Narp mRNA expression previously reported (Tsui et al., supra, 1996). The broadness of the Narp band in brain is consistent with the observation that Narp is glycosylated (Tsui et al., supra, 1996). In non-reducing gels, Narp migrates as a multimer, with a size greater than 220 kDa, consistent with the known ability of members of the pentraxin family to covalently multimerize through disulfide bonds (Emsley et al., *Nature* 367, 338–45, 1994; Gewurz et al., *Curr. Opin. Immunol.* 7:54–64, 1995; Bottazzi et al., *J. Biol. Chem.* 272:32817–23, 1997). Like Narp mRNA expression, Narp protein levels are significantly increased in adult rat hippocampus following seizure induction.

Maximal electroconvulsive seizure (MECS) resulted in a robust increase in Narp protein (8 to 12 fold at 12 hrs; n=2) without a change in the level of the constitutively expressed protein actin. The time course of Narp protein expression is typical for an immediate early gene (IEG) in that it is increased within 30 min of MECS, but is unique among known neuronal IEGs in that it remains elevated for more than 24 hrs. The prolonged increase is not associated with a prolonged increase in mRNA since Narp mRNA returns to basal levels by 8 hrs after MECS (Tsui et al., supra, 1996), suggesting that the Narp protein may be relatively stable. Immunohistochemistry in rat hippocampus showed that Narp protein is expressed in the cell bodies of most neurons throughout the hippocampus, including the dentate gyrus and CA1 region, paralleling the distribution of Narp mRNA (Tsui et al., supra, 1996). Four hours after induction of either MECS or long-term potentiation in vivo, Narp immunostaining showed a large increase throughout the dentate gyms, with little change in CA 1. The hippocampal neuropil was lacking in intense Narp staining except in the hilus of the dentate gyrus, the site of termination of many of the mossy fibers. Of note, hippocampal interneurons, defined by their location and lack of dendritic spines (Buckmaster and Soltesz, *Hippocampus* 6:330–9, 1996), showed a clear dendritic staining pattern that was nearly as intense as that seen in the granule cell layer.

In cultured cells, the anti-Narp antibody recognized a protein with a molecular mass of 54 kD in hippocampal neurons and 58 kD in spinal neurons. Recognition of these proteins by the Narp antibody was blocked by preincubation of the antibody with Narp fusion protein. A second, minor protein at 140 kD was also seen in immunoblots of neuronal cultures, however, this protein was not blocked by preabsortion of the antibody with antigen. The 140 kD protein was not observed in immunoblots of cell surface proteins isolated by surface biotinylation techniques, indicating that it is an intracellular protein, non-specifically recognized by the rabbit serum. Of note, immunoblots of the media overlying neuronal cultures and Narp transfected 293 cells indicated that a substantial amount of Narp was secreted into the media, consistent with the observations of Tsui et al. (supra, 1996), and in keeping with the characteristics of the family of pentraxins.

The immunohistochemical distribution of Narp in cultures of postnatal rat hippocampal neurons, was quite striking, and paralleled and extended the results observed in vivo. Aspiny neurons, which are composed predominantly of inhibitory interneurons (Craig et al., *Proc. Natl. Acad. Sci. USA* 91:12373–7, 1994; Buckmaster and Soltesz, supra, 1996), and make up about one third of the neurons present in these cultures, displayed a somato-dendritic staining pattern for Narp with large superimposed clusters which showed a tight colocalization with GluR1 but not GAD.

Greater than 90% of GluR1 clusters on aspiny neurons had associated Narp staining while only 4 of 111 GAD positive synapses contained Narp. Since our previous, and ongoing, work has shown that dendritic GluR1 clusters are almost always synaptic (defined by synaptophysin immunostaining; O'Brien et al., supra, 1997; Mammen et al., *J. Neurosci.* 17:7351–8, 1997) these results indicate that Narp is localized to excitatory synapses.

The near complete colocalization of Narp and GluR1 on these aspiny neurons was seen at both early and late time points in culture. Moreover the colocalization of Narp with GluR1 was also seen when the anti-Narp antibody was applied to live cultures, implying this is a cell surface phenomenon. Strikingly, the vast majority of spiny, pyramidal neurons had almost no Narp localized to GluR1 clusters in either fixed or live preparations, although bright Narp immunostaining was present in the cell body. A few (less than 5%), scattered spiny neurons did have detectable Narp immunostaining in their spines. Clues to the origin of these latter cells include their large proximal spines and the fact that they were only seen when the oldest postnatal rats (P6–7) were used as a source of cells. Both observations suggest an association with the dentate gyrus. Whether the distinct distribution of Narp in these subtypes of hippocampal neurons is the result of differential synthesis or subcellular transport is, as yet, unresolved.

In addition to the synaptic localization of Narp, many hippocampal axons, identified by Tau immunostaining, were positive for Narp at early time points in culture (45 of 101 on Day 7 in vitro). These axons are likely to be exclusively excitatory, as GAD positive processes were uniformly Narp negative. Axonal staining was only seen in permeablized preparations. Narp staining, both live and permeablized, was blocked by preabsortion of the Narp antibody with antigen, confirming its specificity.

In cultured spinal neurons, which are almost all aspiny, clusters of Narp immunostaining were more widespread, and were seen to co-localize with the AMPA receptor subunit GluR1 in most cases. Surface Narp immunostaining was seen to colocalize with synaptic GluR1 immunostaining but was not present in synapses devoid of GluR1, which we have previously shown to be inhibitory synapses (O'Brien et al., supra, 1997). Narp clustering at excitatory synapses was also observed when the Narp antibody was applied to fixed and permeablized preparations. Overall 73% (529/720) of GluR1 clusters had associated Narp immunostaining, both in live and fixed preparations. In contrast, surface Narp rarely co-localized with inhibitory synapses (12/218) identified by presynaptic GAD immunostaining. As in hippocampal cultures, Narp immunostaining was also observed in a subset of Tau immunopositive axons at early time points, although its appearance was more clumped than that seen in hippocampal axons. Of note, surface staining with the Narp antibody in early spinal cultures frequently revealed, a few scattered, non-synaptic, dendritic, Narp clusters, which, in contrast to synaptic Narp clusters, were only variably associated with GluR1).

Example 2

Transfected Narp Accumulates at Excitatory Synapses

In order to characterize the synaptic targeting of Narp in neurons, a C-terminal myc-tagged version of Narp (designated myc-Narp) was transfected into cultured spinal neurons (Dong et al., *Nature* 386:279–84, 1997). After 72 hours of expression, live staining with an anti-myc (mouse) antibody, followed by a FITC labeled anti-mouse secondary, was used to reveal the surface distribution of the transfected Narp. Subsequent staining of the same cells, after fixation and permeabilization, with an AMCA labeled anti-myc (rabbit) antibody was used to identify transfected neurons and their axons and dendrites, while GluR1 and GAD staining were used to identify excitatory and inhibitory synapses, respectively.

Staining of transfected neurons indicated that myc-Narp, similar to endogenous Narp, was distributed throughout the somato-dendritic domain of the transfected neuron and was also specifically localized to excitatory synapses. In a series of 3 separate experiments, 74% (123/167) of GluR1 clusters on 34 transfected neurons had clear clusters of surface myc-Narp stain. Like in untransfected neurons, nearly all GluR1 clusters in transfected neurons are synaptic (i.e., associated with synaptophysin or synapsin 1 staining). Conversely, myc-Narp staining in transfected neurons rarely (18/114) co-localized with presynaptic GAD staining. In addition to the clusters of transfected Narp associated with GluR1, a slightly smaller number of myc-Narp clusters were also seen that were not associated with GluR1. It is likely that these are similar to the extrasynapic Narp clusters see in non transfected cells. Whether these represent Narp in the process of migrating to excitatory synapses, or represent a form of Narp available to interact with nascent excitatory terminals is yet to be determined.

To exclude the possibility that the live staining technique induced the aggregation of myc-Narp at excitatory synapses, the co-localization of myc-Narp with GluR1 was examined in neurons fixed before staining. In these transfected neurons, 86% (266/309) of the dendritic GluR1 clusters were associated with focally clustered myc-Narp staining.

Example 3

Synaptic Narp is Derived from Both the Presynaptic and Postsynaptic Neuron

Since only 1 to 3% of the neurons in a given experiment are transfected by the procedure described above, it was relatively easy to distinguish myc-Narp that came from the postsynaptic cell (surface stain associated with the large proximal processes of an isolated transfected cell) from myc-Narp originating from the presynaptic cell (surface stain associated with a solitary thin process coursing over a non-transfected cell body or dendrite which is not in continuity with any visibly transfected cell). This operationally defined distinction between axon and dendrite was verified to be nearly 90% specific in pilot experiments in which labeled processes were stained with anti-Tau antibodies to distinguish axons from dendrites. As discussed above, 74% of excitatory synapses in transfected neurons had clear surface myc-Narp stain, indicating that Narp is targeted to the synapse from the postsynaptic neuron. However, additional observations suggested that Narp was also targeted to the synapse from the presynaptic terminal. Myc-Narp positive processes were frequently observed far removed from any transfected neuronal cell bodies (autaptic connections between Narp positive axons and dendrites were uncommon). Parallel studies revealed that these processes were axons, as 80 of 91 such processes were strongly positive for the axon specific protein Tau. Nearly all the myc-Narp containing axons were immunonegative for GAD, suggesting that niyc-Narp, like endogenous Narp, is not transported down the axons of GABAergic neurons. Thus, presynaptic myc-Narp was largely restricted to axons of excitatory neurons. This pattern of axonal staining is reminiscent of the endogenous Narp positive axons seen in early spinal arid hippocampal cultures. When myc-Narp containing axons contacted a GluR1 positive, non-transfected neuron, 37 of 48 such contacts were associated with at least one GluR1 cluster. Clusters were invariably seen at sites where live myc-Narp staining revealed extracellular myc-Narp (for example, in one microscopic field 54 myc-Narp clumps were associated with 51 GluR1 clusters). These observations indicate that the myc-Narp transgene is derived from the presynaptic element.

Electron microscopy from rat hippocampus confirmed and extended many of the observations made with light microscopy in vivo and in vitro. Immunogold labeling was found in presynaptic terminals, and was especially prevalent in mossy terminals of the hilus and CA3 stratum lucidum, although labeling was also seen in other areas of the hippocampus. Presynaptic gold was often seen in the region of synaptic vesicles. Gold also was found in synaptic clefts and

*Immunol.* 7:54–64, 1995; Bottazzi et al., *J. Biol. Chem.* 272:32817–23, 1997), the possibility that Narp may function to facilitate the formation of excitatory synapses was explored. Thus, the number of synaptic GluR1 clusters (i.e., GluR1 clusters associated with synaptophysin staining) in transfected neurons over expressing myc-Narp was compared with the number of synaptic GluR1 clusters in untransfected neurons or in neurons transfected with a control plasmid containing the C-terminus of the NMDA receptor subunit NR1A (NR1CT).

In five transfection experiments, the number of synaptic GluR1 clusters on Narp transfected neurons was increased 1.9 fold compared to either control (Table 1; $p<0.01$). A similar increase in the total number of synaptophysin clusters (synapses) per neuron was observed in Narp transfected neurons. No change was noted in the number of GAD positive terminals on Narp transfected neurons or in the size of the visualized neuritic field of Narp transfected neurons. Interestingly, no increase in non-synaptic GluR1 clusters was noted.

TABLE 1

The effect of NARP overexpression on cultured spinal neurons.

| | NARP Transfected | | NR1CT Transfected | |
|---|---|---|---|---|
| | Transfected | Untransfected | Transfected | Untransfected |
| Synaptic GluR1 Clusters | 13.0 +/− 3.8** (n = 59) | 7.4 +/− 1.2 (n = 77) | 6.9 +/− 1.4 (n = 51) | 6.1 +/− 1.3 (n = 71) |
| Synaptophysin Clusters | 16.0 +/− 4.6* (n = 59) | 11.8 +/− 1.2 (n = 77) | 10.9 +/− 2.3 (n = 51) | 10.5 +/− 1.6 (n = 71) |
| Neuritic Length (μm) | 225 +/− 51 (n = 32) | — | 220 +/− 60 (n = 33) | — |
| GAD Clusters | 5.9 +/− 3.9 (n = 40) | 5.4 +/− 2.8 (n = 37) | 6.3 +/− 3.2 (n = 33) | 6.0 +/− 2.1 (n = 43) |

Cultured spinal neurons were transfected with either a myc-tagged NARP or NRICT construct as described in Methods. The number of synaptic GluR1 clusters as well as the number of total synapses were calculated in transfected and non-transfected neurons in each condition in a series of 5 experiments. The calculation of neuritic length was taken from a subset of 3 of the 5 experiments and was determined using the permeablized myc stainingat 100× (No attempt was made to distinguish axons from dendrites or to measure the entire neuritic length). In a separate series of 3 experiments, the number of GAD clusters on similarly transfected neurons were calculated.
Numbers are expressed as +/− S.D of the mean for each experiment.
**$P < .01$ (paired) for all comparisons.
*$P < .05$ (paired) for all comparisons.

postsynaptic densities. In general, postsynaptic labeling was not as dense as presynaptic labeling. In controls in which the primary antibody was preadsorbed with fusion protein, gold was very uncommon in presynaptic or postsynaptic structure; and was absent in the synaptic cleft. The surprising occurrence of pre and postsynaptic Narp in spines of the dentate gyms in vivo contrasts with results in vitro where spiny Narp staining was decidedly uncommon. One possible explanation for this discrepancy lies in the postnatal development of the dentate gryus (Bayer and Altman, *J. Comp. Neurol.* 158::55–79, 1974) where much of the spiny Narp immunostaining was seen in vivo. These cells would be under represented in cultures taken from perinatal animals. Alternatively, the relative sensitivities of the two techniques may differ.

Example 4

Over Expression of Narp Increases the Number of Excitatory Synapses in Cultured Spinal Neurons Given the presence of Narp on both pre and postsynaptic processes and the biochemical propensity of pentraxins to form head to head multimeric aggregates (Emsley et al., *Nature* 367, 338–45, 1994; Gewurz et al., *Curr. Opin.*

Example 5

Narp Clusters the AMPA Receptor Subunits GLUR1–3 In Transfected 293 cells

The clustering of AMPA receptors is a major characteristic of excitatory synapse formation. To investigate the possible role of Narp in AMPA receptor clustering (similar to rapsyn aggregating nicotinic acetylcholine receptors at the neuromuscular junction; see Phillips et al., *J. Cell. Biol.* 115:1713–23, 1991; Ramarao and Cohen, *Proc. Natl. Acad. Sci. USA* 3:4007–12, 1998), the ability of Narp to aggregate AMPA receptors was investigated. When expressed alone, Narp (or myc-tagged Narp) forms large surface aggregates which can be seen in live or permeablized preparations. These same surface clusters are also seen when an Fab fragment of the anti-myc antibody is used on live preparations. Moreover, using a marker for transfected cells, surface Narp staining was only seen in transfected cells, and was not the result of non-specific binding of secreted protein to untransfected cells. In contrast to Narp, GluR1 is normally distributed diffusely either in live or fixed preparations.

Co-expression of GluR1 with Narp induced GluR1 to form large surface aggregates which co-localized with the Narp clusters. These Narp-GluR1 aggregates were seen either with surface staining using whole antibody or Fab fragments, or in fixed and permeablized preparations. In addition to GluR1, Narp induced aggregates of GluR2 and GluR3 but not GluR4, GluR6, NR1, NR1/2A or the neuronal glutamate transporter EAAC1. Of note, preliminary electrophysiological studies in transfected 293 cells showed no differences in AMPA receptor current amplitudes or desensitization kinetics in the presence or absence of co-expressed Narp.

Example 6

NARP Co-Immunoprecipitates with AMPA Receptor Subunits in Both 293 Cells and Brain Co-immunoprecipitation experiments were used to examine whether Narp is physically associated with AMPA receptors in HEK-293 cells. Immunoprecipitation of Narp demonstrated that Narp was specifically associated with the GluR1, GluR2 and GluR3 subunits in co-transfected cells. Interestingly, treatment of transfected cells with 1 mM tunicamycin had no effect on the association between Narp and any of the AMPA receptor subunits, implying that the lectin property of Narp (Tsui et al., supra, 1996) does not mediate its interaction with AMPA receptor subunits.

To determine whether Narp is associated with AMPA receptors in vivo, co-immunoprecipitation experiments were performed from rat brain. As in the HEK cells, Narp was found to be specifically associated with GluR1 when either anti-Narp or anti-GluR1 antibodies were used to isolate the complex. The co-immunoprecipitation of Narp and GluR1 was blocked by preincubating the initial antibody with its cognate peptide, and no immunoprecipitation was seen with preimmune serum. These studies suggest that Narp and GluR1–3 could directly interact. Furthermore, their association in 293 cells indicates that other neural-specific proteins are not required for these interactions to occur.

Example 7

NARP Induces the Aggregation of AMPA Receptor Subunits in Apposing Cells

To evaluate whether Narp could mediate intercellular aggregation of GluR1, similar to that expected at a synapse, myc-tagged Narp and GluR1 were expressed separately in 293 cells and subsequently co-cultured together. Under these conditions, surface Narp clusters on one cell could induce large surface GluR1 aggregates on another. In a total of 109 contacts between a GluR1 expressing transfected cell and a Narp expressing cell, there was a mean of 1.2+/−0.75 large overlapping GluR1/myc-Narp clusters at these sites of contact. The specificity of the interaction between GluR1 and Narp was evidenced by the fact that Narp did not induce clusters of either the neuronal glutamate transporter EAAC1 (0.04+/−0.05; n=121) or the NMDA receptor subunits NR1 and NR2A (0 coclusters; n=32 contacts). Moreover, the number of GluR1 clusters at sites of contact with non-Narp expressing 293 cells was extremely low [0.07 R1 clusters per contact with a GluR2 expressing cell (n=76); 0.03 R1 clusters per contact with a Pick1/GluR2 expressing cell (n=58)]. The interaction between GluR1 and Narp required contact between the heterologous cells, as there was no evidence that Narp could diffuse from one cell and induce GluR1 clusters on another.

These results indicate that Narp and GluR1 do not need to be expressed in the same cell for AMPA receptor aggregation to occur. However, when untagged Narp was co-expressed with GluR1 and then co-cultured with cells expressing only myc-tagged Narp, there was a greater than two fold increase in the number of intercellular myc-Narp*GluR1 co-clusters (mean 2.6+/−1.4 n=124; p<0.01). This suggests that the expression of Narp in both the "pre-" and "postsynaptic" cell facilitates cluster formation. The effect of co-expressed Narp on the incidence of intercellular Narp-GluR1 clusters occurred in the absence of any effect on the expression/accumulation of GluR1. To ensure that the surface staining technique did not induce the intercellular co-clustering of GluR1 and Narp, we examined the co-localization of GluR1 and Narp in cells fixed and permeablized prior to staining, as well as in cells in which live staining was done with an Fab fragment to prevent antibody induced aggregation. In all cases the results were identical, both for the ability of Narp to cluster AMPA receptors on apposing cells, and for the coexpression of Narp with GluR1 in the "postsynaptic" cell to potentiate this process.

Example 8

NARP Clusters GLUR1 in Cultured Spinal Neurons

Although Narp is secreted from transfected 293 cells and can be collected from the media, it appeared to have no bioactivity in this form, assayed by its ability to bind to other 293 cells transfected with Narp and/or GluR1. Moreover this soluble form of Narp did not bind to cultured spinal neurons and did not cluster glutamate receptors on these cells. However, the bioactivity of Narp could be readily demonstrated when 293 cells expressing myc-Narp on their surface were mixed with spinal neurons previously grown in culture for 4 days. The neurons and transfected HEK-293 cells were cocultured for 48 hours and then fixed and stained for myc-Narp, GluR1 and synapsin. When contacts between myc-Narp expressing 293 cells and GluR1 expressing spinal neurons were examined for overlapping myc-Narp/GluR1 clusters, 64% (82/128) of the myc-Narp clusters in contact with the neuron overlapped with neuronal GluR1 clusters (mean of 2.6+/−1.5 overlapping myc-Narp/GluR1 clusters per 293-neuron contact).

Only 5 of the 82 GluR1 clusters associated with myc-Narp had any staining for the synaptic vesicle protein synapsin 1 compared with native GluR1 clusters which almost always (90%) co-localize with synapsin (146/163 on day 6). These results strongly suggest that the myc-Narp transfected 293 cells induced the non-synaptic GluR1 clusters rather than associated with established synaptic GluR1 clusters. To control for random GluR1 clusters which might occur at sites of contact between 293 cells and spinal neurons, 293 cells were transfected with a combination of Pick1 and GluR2, which also form large aggregates on the surface of 293 cells (Xia et al., Neuron 22:179–187, 1999). No clusters of neuronal GluR1 were seen associated with these Pick1/GluR2 clusters at a total of 58 cell—cell contacts involving 88 Pick 1 clusters. Moreover there was no evidence that contact with an untransfected 293 cell or a 293 cell transfected with a diffusely expressed construct (such as GluR2) could cluster GluR1 on the contacted dendrite. As a sign of specificity, Narp transfected 293 cells did not cluster the NMDA receptor subunit NR1 or the neuronal glutamate transporter EAAC1. In addition to the typical overlapping clusters of myc-Narp and GluR1 at contact points between neurons and 293 cells, clusters of myc-Narp which appeared to have broken off from processes of 293 cells were also capable of clustering GluR1. Although the number of these latter aggregates were not formally tabulated, they appeared to be at least as numerous as those still obviously in contact with the 293 cell. We did not see an ingrowth of axons into the transfected 293 cells. The reasons for this discrepancy is not certain but it is possible that axons avoided the 293 cells (transfected or not).

Thus, it has been determined that the neuronal IEG Narp is selectively expressed at the majority of excitatory, axo-dendritic shaft synapses on (aspiny spinal cord and hippocampal neurons in vitro. In addition, a small number of spine bearing neurons express Narp at their excitatory synapses in culture. In vivo, immunoelectronmicroscopy confirms Narp to be present at both pre- and postsynaptic sites of spiny and aspiny synapses. The prominent presynaptic localization of Narp in mossy fiber terminals is associated with synaptic vesicles. It has been further demonstrated that Narp is capable of clustering AMPA receptors and that this clustering activity involves a physical interaction (direct or indirect) with AMPA receptor subunits. Because Narp is dramatically upregulated in neurons in response to patterned synaptic activity and is expressed at relatively high levels in developing and adult brain (Tsui et al., supra, 1996), the studies suggest that Narp may play an critical role in linking activity with the Development of plasticity and excitatory synapses.

The predominant expression of Narp at axo-dendritic shaft synapses in vitro infers highly specific cellular expression and subcellular targeting. Narp appears to be targeted to synapses from both the pre- and postsynaptic cell. Evidence for specific presynaptic localization is provided both by electron microscopy (EM) and by the observation that Narp is expressed in a subset of axons in both native and transfected cells. Strong endogenous Narp staining is seen in axons in both hippocampal and spinal neurons. The fact that none of these axons show staining for GAD, a marker for GABAergic interneurons which comprise approximately 25% of the neurons in spinal cultures (O'Brien et al., 1997) and 30% of the neurons in these postnatal hippocampal cultures, suggests that Narp is transported only into the axons of glutamatergic neurons. Furthermore, in transfected neurons, epitope tagged Narp is only seen in GAD negative axons where it becomes externalized exclusively at excitatory terminals. Narp is also present on the dendritic surface of native and transfected neurons at both synaptic and non-synaptic sites. The synaptic localizations are most dramatic and are notably specific for excitatory synapses.

The pattern of glutamate receptor clustering in hippocampal interneurons in vitro appears somewhat similar to that observed in spinal neurons, and different from spiny pyramidal cells. The fact that a molecular difference may exist in the aggregating molecules expressed at excitatory shaft and spine synapses is not surprising. In cultured hippocampal neurons, pyramidal cell spine synapses are highly enriched in NMDA receptors, in contrast to dendritic shaft synapses on aspiny interneurons and spinal neurons, which are more heavily weighed towards AMPA receptors (O'Brien et al., supra, 1997; Rao et al., J. Neurosci. 18:1217–29, 1998; Liao et al., Nature Neuroscience 2, 3743, 1999). In addition, the actin cytoskeleton (Alkon et al., J. Neurosci. 18:2423–36, 1998), the distribution of the Rho target citron (Zhang et al., J. Neurosci. 19:96–108, 1999), and the modulation of AMPA receptors by activity and BDNF (Rutherford et al., Neuron 2:521–30, 1998), all appear different in spiny and aspiny hippocampal neurons. Interestingly, the major excitatory input onto hippocampal interneurons is through the granule cells of the dentate gyrus (Accsady et al., J. Neurosci. 18:3386–3403, 1998) the region most enriched in Narp protein and mRNA (Tsui et al., supra, 1996). Sprouting and synaptogenesis are documented to occur in terminal mossy fibers following seizure (Cavazos et al., J. Neurosci. 11:2795–803, 1991) and may involve the activity of molecules such as Narp which are strongly induced by seizures. In vivo, the distribution of Narp by immuno-electron microscopy appears to be more widespread amongst excitatory synapses than our data in vitro would indicate, with spine as well as shaft accumulation.

The family of long pentraxins, of which Narp is a member, has several characteristics which might play a role in promoting excitatory synapse formation. Included among these are the ability to form side to side and head to head multimeric aggregates (Bottazzi et al., J. Biol. Chem. 272: 32817–23, 1997; Emsley et al., Nature 367, 338–45, 1994; Goodman et al., Cytokine Growth Factor Rev. 2: 191–202, 1999, and the ability to bind other proteins via a lectin like domain. When assayed by non-reducing SDS-PAGE, native Narp migrates with an apparent size of >200 kDa and this mobility shifts to ~55 kDa with addition of reducing agent, consistent with the prediction that Narp forms cysteine-linked multimers. These multimers however are far below the size of the large macroaggregates seen on the surface of transfected cells, a property unique to Narp among the family of pentraxins. It is possible that an additional domain in the unique N-terminus mediates the formation of these macroaggregates. The ability of Narp to cluster AMPA receptors would not have been predicted from a knowledge of the family of pentraxins, since the association of Narp with AMPA receptor subunits in the presence of tunicamycin suggests that it is not the lectin component of Narp which mediates this interaction. Indeed, the specificity of the interaction (GluR1–3 but not GluR4, 6, and NR1) would also argue against a non-specific interaction such as that mediated by a lectin.

Given the localization of Narp at excitatory synapses, its AMPA clustering activity may play an important role in the synaptic aggregation of those receptors. Biochemical and immunohistochemical characterization demonstrates the specificity of the interaction between Narp and AMPA receptor subunits. When viewed in the context of other glutamate receptor clustering molecules, Narp displays several novel features. In contrast to the intracellular proteins PSD-95 and GRIP, Narp is an extracellular molecule with no PDZ domains and no access to intracellular domains on AMPA receptor subunits. These results suggest that if Narp directly interacts with AMPA receptor subunits, it interacts with extracellular domains on these proteins. Narp's ability to form large aggregates contrasts with the pattern seen with PSD-95, which by itself is diffusely expressed (Kim et al., 1996). Like rapsyn (Ramarao and Cohen, 1998) and Pick1 (Xia et al., 1999), Narp has coiled-coil domains in its unique N-terminus (Tsui et al., 1996), which may be available for interaction with extracellular components of GluR1–3 as well as for Narp—Narp interactions. It is very likely that Narp directly interacts with AMPA receptor subunits. Although unlikely, the presence of an additional linker molecule in both neurons and HEK-293 cells has not been completely ruled out.

Another notable functional property of Narp expressing cells is their ability to cluster AMPA receptors on apposing cells, even when the contacted cell does not express Narp. In view of the documented physical interaction between Narp and AMPA receptors when these proteins are expressed in the same cells, it seems likely that the intercellular clustering activity also involves their physical interaction. The transcellular clustering activity of Narp is further enhanced when the apposing cell co-expresses Narp with AMPA receptors, suggesting that a Narp—Narp interaction may also contribute to transcellular clustering. In this regard, Narp may potentially display similarities with cadherins, which self associate and participate in synaptogenesis from both the pre and postsynaptic surfaces (Fannon and Colman, *Neuron* 17:423–34, 1996; Uchida et al., *J. Cell. Biol.* 135:767–79, 1996). Unlike the family of cadherins, however, Narp appears to be completely extracellular with no transmembrane domain (Tsui et al., supra, 1996). Moreover, direct proof that Narp functions as an adhesion molecule is lacking. The hypothesized function of Narp to transynaptically aggregate AMPA receptors is unique but reconcilable when considering that synaptic distances in the CNS are small due to the lack of a well defined basement membrane (Gordon-Weeks et al., *Exp. Physiol.* 77:68 1–92, 1992), and that Narp is likely to be secreted and may bind postsynaptic proteins at an intermediary point between the two cells. EM localization shows Narp in the synaptic cleft, and are consistent with this proposed function.

A model in which Narp—Narp interactions between pre- and postsynaptic cells contribute to excitatory synapse formation with a secondary, clustering of synaptic AMPA receptors due to Narp-AMPA receptor interactions is proposed. In support of a "presynaptic" effect of Narp, one should note that Narp expressed on heterologous cells induces AMPA receptor clusters on neurons. By contrast, a "postsynaptic" effect of Narp is suggested by the observation that when Narp expression is upregulated by transfection, it results in a two fold increase in the number of excitatory synapses, with no change in the number of inhibitory synapses. Since only a small percentage of cells are transfected in this experiment, the increase in number of excitatory synapses on transfected cells as compared with non-transfected cells in the same dish argues strongly for a postsynaptic action of Narp. The synaptogenic effect of upregulated Narp expression in neurons would be a manifestation of the potentiating effect of Narp on transcellular cluster formation seen in heterologous cells when Narp is co-expressed with AMPA receptor subunits. It is also possible that excess Narp in the postsynaptic neuron promotes Narp—Narp intercellular interactions with presynaptic elements and makes it more favorable for the over expressing cell to attract new synapses. This would favor excitatory synapses over inhibitory synapses, since inhibitory axons do not appear to express Narp. Preliminary observations suggest that the small extrasynaptic clusters of Narp seen in native and transfected cells lack an association with GluR1. It may be that only the large Narp clusters seen at synapses or in 293 cells are able to recruit AMPA receptors, perhaps due to interacting domains on Narp. Further analysis of the structure-function relationship for Narp should help reveal all the mechanisms that contribute to synaptogenesis.

Several attempts have been made to disrupt endogenous synaptogenesis using one anti-Narp antibody. However, the anti-Narp antibody currently available does not appear to be a blocking antibody up to a concentration of 30 mg/ml either in spinal cord cultures or in the 293 cell assay. More antibodies will be developed. Antisense oligonucleotides directed to several sites on Narp have had no effect on Narp production assayed by immunoblots and immunohistochemistry. Other antisense oligonucleotides are currently being studied to produce agents that inhibit Narp expression. Further investigations will also be made into the soluble form of Narp.

Narp provides further evidence that the neuronal IEG response can directly modify synaptic function. Other examples include Homer, which regulates the coupling of synaptic group 1 metabotropic glutamate receptors to inositol trisphosphate receptors (Tu et al., *Neuron* 21.717–726, 1998), RGS2 which regulates coupling of specific G-protein linked receptors to their down stream signaling cascade (Ingi et al., *J. Neurosci.* 18:7178–88, 1998), Cox-2, which is the nodal enzyme in prostaglandin synthesis (Kaufmann et al., *Proc. Natl. Acad. Sci. USA* 93, 2317–21, 1996: Yamagata et al., *Neuron* 11:371–86, 1993), and Arc (Lyford et al., *Neuron* 14, 433–45, 1995; Steward et al., *Neuron* 21:741–51, 1998), which may function as an adapter protein for CaMKII. One of the challenges in describing the contribution of IEGs to long-term synaptic plasticity is to understand how a genomic response, that is temporally and spatially remote from an "activated" synapse, can selectively modify the function of specific synapses. Emerging evidence suggests that IEG products may be targeted to specific active synapses. For example, Arc mRNA selectively accumulates at dendritic sites of recent synaptic activity (Steward et al., *Neuron* 21:741–51, 1998). The present studies suggest an alternative mechanism that could mediate synapse-specific effects of Narp. Presynaptic secretion of Narp at active synapses could target its action to specific synapses where it could cluster, or perhaps stabilize, GluRs and thereby selectively strengthen active synapses. Thus Narp provides new tools to study the mechanisms of synapse-specific and protein synthesis-dependent neuronal plasticity.

It is to be understood that while the invention has been described in conjunction with the detailed description thereof, the foregoing description is intended to illustrate and not limit the scope of the invention, which is defined by the scope of the appended claims: Other aspects, advantages, and modifications are within the scope of the following claims.

What is claimed is:

1. A method for identifying a compound which affects the formation of AMPA receptors into aggregates, comprising:
   (a) incubating a test compound and a pre-synaptic cell expressing a long pentraxin under conditions sufficient to allow the compound to interact with the cell, wherein the long pentraxin is Narp or NP-1;
   (b) determining the effect of the compound on the formation of AMPA receptors into aggregates in said pre-synaptic cell or in a post-synaptic cell synapsing with said pre-synaptic cell; and
   (c) comparing the formation of AMPA receptors into aggregates of said pre-synaptic cell contacted with said compound, or in said post-synaptic cell not contacted with said compound or a post-synaptic cell synapsing with said pre-synaptic cell not contacted with said compound.

2. The method of claim 1, wherein the compound is a long pentraxin polypeptide.

3. The method of claim 1, wherein the effect is inhibition of the formation of AMPA receptors into aggregates.

4. The method of claim 1, wherein the effect is stimulation of the formation of AMPA receptors into aggregates.

5. The method of claim 1, wherein the AMPA receptor comprises a subunit selected from the group consisting of a GluR1, GluR2, and a GluR3 subunit.

6. The method of claim 1, wherein said compound is selected from the group consisting of peptides, peptidomimetics, polypeptides, pharmaceuticals, chemical compounds, nucleic acids, antibodies, neurotropic agents and anti-epileptic agents.

7. A method for identifying a compound which affects the formation of AMPA receptors into aggregates, comprising:
   (a) incubating the compound and a pre-synaptic cell expressing a polynucleotide that encodes the polypeptide of SEQ ID NO:2, under conditions to allow the compound to interact with the cell;
   (b) determining an effect of the compound on the formation of AMPA receptors into aggregates in said pre-synaptic cell or in a post-synaptic cell synapsing with said pre-synaptic cell; and
   (c) comparing the formation of AMPA receptors into aggregates of said pre-synaptic cell contacted with said compound, or in said post-synaptic cell, with the formation of AMPA receptors into aggregates in a pre-synaptic cell not contacted with said compound or a post-synaptic cell synapsing with a pre-synaptic cell not contacted with said compound, thereby identifying a compound which affects the formation of AMPA receptors into aggregates.

8. The method of claim 7, wherein the effect is inhibition of the formation of AMPA receptors into aggregates.

9. The method of claim 7, wherein the effect is stimulation of the formation of AMPA receptors into aggregates.

* * * * *